United States Patent [19]

Miller

[11] 4,041,943

[45] Aug. 16, 1977

[54] CONTROL APPARATUS FOR VARIABLE REGULATION OF LUNG INFLATION HOLD TIME

[76] Inventor: Bruce B. Miller, 714 Ashley Drive, Kalamazoo, Mich. 49001

[21] Appl. No.: 607,103

[22] Filed: Aug. 25, 1975

[51] Int. Cl.² .............................................. A61M 16/00
[52] U.S. Cl. ................................................... 128/145.8
[58] Field of Search ........................... 128/145.5–145.8, 128/146.5

[56] References Cited

U.S. PATENT DOCUMENTS

| 2,121,311 | 6/1938 | Anderson et al. | 128/145.8 |
| 3,124,124 | 3/1964 | Cross | 128/145.5 |
| 3,915,164 | 10/1975 | Bird | 128/145.8 |

Primary Examiner—Robert W. Michell
Assistant Examiner—Henry J. Recla
Attorney, Agent, or Firm—Ian C. McLeod

[57] ABSTRACT

A control apparatus is described which can be incorporated into conventional intermittent positive breathing gas pressure lung treatment systems to provide for holding the gas in the lungs for a brief period of time after inspiration and before expiration. The control apparatus in the system delays the opening of a gas pressure release opening exhaust valve associated with the patient breathing portion of the system. The apparatus enables such systems to more closely simulate normal breathing and to increase the time during which vaporized medication supplied in the breathing gas can be absorbed in the lungs.

4 Claims, 3 Drawing Figures

CONTROL APPARATUS FOR VARIABLE REGULATION OF LUNG INFLATION HOLD TIME

SUMMARY OF INVENTION

The present invention relates to a control apparatus for introducing a variable regulation of lung inflation hold time into intermittent positive pressure treatment of the lungs. In particular, the present invention relates to the control apparatus provided in a conventional prior art respiration system to produce the hold time.

PRIOR ART

Systems are being marketed for intermittent positive breathing gas pressure lung treatment. These systems include a respirator connected to a breathing gas source and connected to a breathing apparatus around the mouth (and sometimes the nose) which intermittently provides a positive gas pressure to inflate the lungs during the inspiratory phase of the breathing cycle. When the time for inspiration is completed, the gas pressure is eliminated and the gas in the lungs is expired through an exhaust valve in the breathing apparatus by the natural force of the diaphragm in the body. During the inspiratory phase, the exhaust valve is closed by the gas pressure from the respirator on a pressure activated diaphragm in the valve. When the gas pressure is released from the diaphragm, passive exhalation is allowed to occur. The problem with such systems is that as soon as the inspiratory phase is completed, the expiratory phase begins upon opening of the exhaust valve. For this reason, such systems, have been criticized for not providing a period for allowing the gas to be held in the lungs before the exhaust valve opens and the expiratory phase begins.

It is therefore an object of the present invention to provide a control apparatus which can be used in intermittent positive pressure systems to provide an inflation hold time period before the exhaust valve opens. It is further an object of the present invention to provide a control apparatus which is economical to build and highly reliable in service. These and other objects will become increasingly apparent by reference to the following description and the drawing.

DETAILED DESCRIPTION OF INVENTION

The present invention relates to an improvement in a system used for intermittent positive pressure lung treatment wherein a respirator means for regulating the gas pressure from a gas source is connected by a first gas line to a breathing element for providing the gas to the lungs upon inspiration and wherein a pressure sensitive exhaust valve for allowing elimination of the gas upon expiration from the lungs is connected to the breathing element and to the respirator by a second gas line and is opened at the pressure limit established by the respirator when the pressure is released by the respirator which causes the valve to open, which comprises a one way check valve mounted in a housing and connected into the second gas line so as to have an upstream side connected to the respirator and a downstream side connected to the exhaust valve with a vent on the downstream side of the housing having a constriction for controlling gas flow out the vent, such that there is a delay in the opening of the exhaust valve due to gas pressure in the valve which holds the gas in the lungs for a period of time until the gas bleeds through the constriction. The control apparatus comprises a one way check valve mounted in a housing so as to have an upstream side and a downstream side; gas coupling means for connecting the upstream side to a respirator gas supply; a gas second coupling means for connecting the downstream side to an exhaust valve controlling a breathing element for release of gas from the lungs; and a vent on the downstream side of the housing having a constriction for controlling the gas flow out of the vent, thus controlling the pressure at the second coupling means for a period of time until gas in the downstream side bleeds through the constriction.

The term "constriction" as used in this specification and claims means an opening in a conduit to a lower gas pressure which allows for the bleeding of a higher gas pressure over a period of time from the exhaust valve control side of the system. The constriction can be supplied by orifices which may be replaceable or by a needle valve which provides a variable gas passage.

Pulmonary-physiology dictates that the breathing pattern of humans in different from the actual function of these systems in that some inflation hold is inherent within our breathing pattern. The variable-lung inflation hold time control apparatus simulates this more natural breathing pattern in patients who are receiving intermittent positive pressure breathing theraphy.

Figure 3:
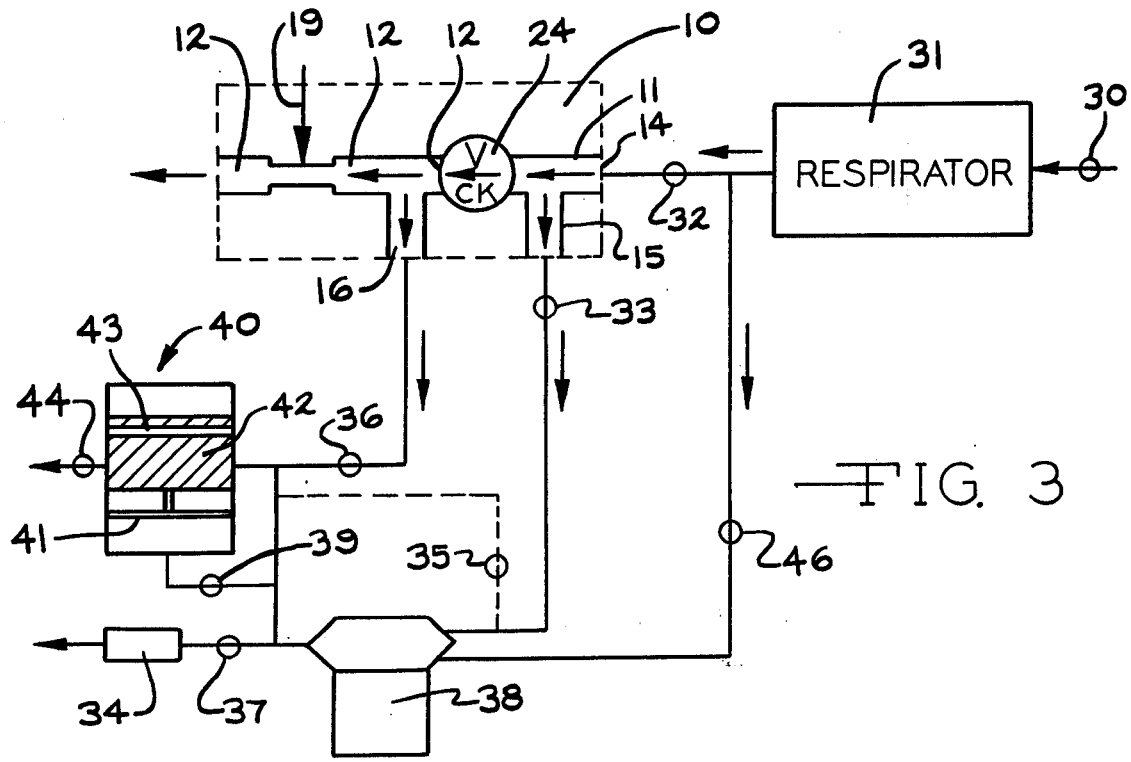
FIG. 3 is a schematic view of the control apparatus of the present invention incorporated in an intermittent positive pressure system.

Referring first to FIG. 3, in prior art systems an inlet gas line 30 is connected to a respirator 31 without the control element 10 or line 36. From the respirator 31, a conduit (shown as 32 and 33) is connected to a breathing tube 34 (shown as a dotted line) via conduit 35 to the breathing tube 34. Conduit 35 is also connected via conduit 39 to an exhaust valve 40. The exhaust valve 40 includes a diaphragm 41, activated via conduits 35 and 39, connected to a movable piston 42 which has an opening 43 which is closed when the diaphragm 41 is pressurized (as shown). The patient's lung pressure upon the end of inspiration, when the pressure on the diaphragm 41 from the line 36 is released, moves the piston 42 to open the line 37 to exhaust at 44 through opening 43.

At the beginning of the inspiratory phase, the exhalation valve 40 is closed down via pressure applied across the top of a diaphragm 41. During the expiratory phase, the flow of gas through the nebulizer drive lines 32, 33, 35 and 37 ceases, pressure drops and the exhaust valve 40 vents allowing the patient to immediately exhale passively.

Figure 1:
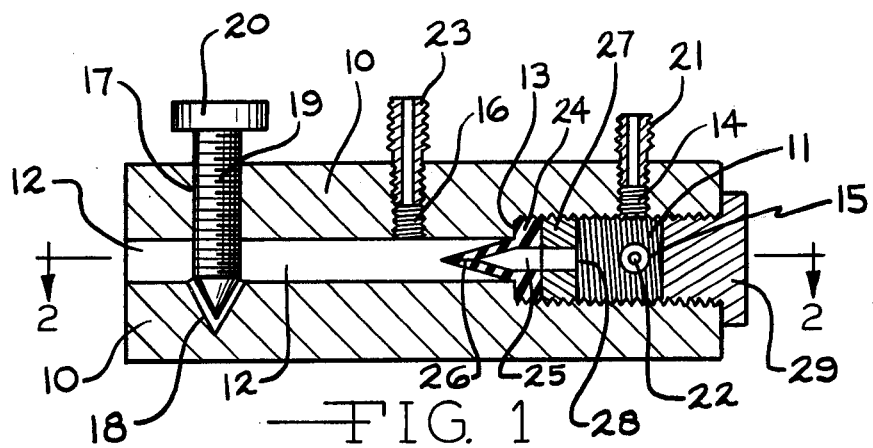
FIGS. 1 and 2 are front and plan cross-sectional views, respectively, of the variable inflation hold control apparatus of the present invention.
Figure 2:
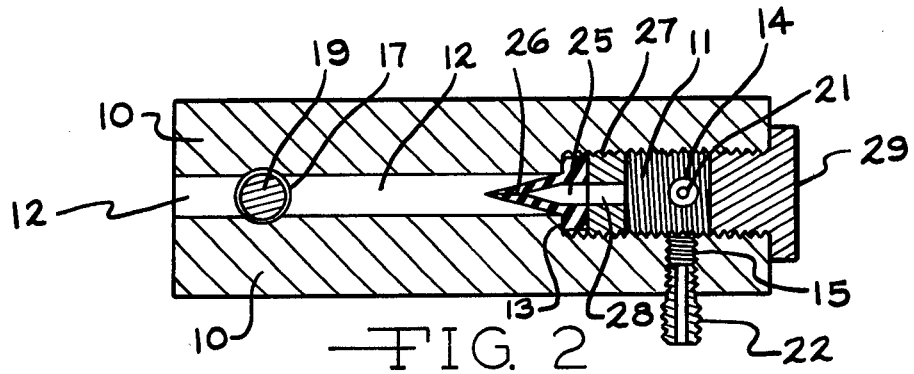

Referring to FIGS. 1 and 2, a preferred form of the variable inhalation or inflation hold time control apparatus as a separate unit is shown. A housing 10 is provided with an internally threaded hole 11 part of the way into the housing 10. A smaller diameter hole 12 is provided the rest of the way through the housing 10 and is connected to the threaded hole 11 such that a shoulder 13 is provided between them. Leading into the larger hole 11 at right angles are two threaded holes 14 and 15. Leading into the smaller hole 12 are two threaded holes 16 and 17. The hole 17 closest to the exit from the housing 10 is centered on a seat 18 which with a needle valve 19 acting as a gas regulation orifice in the hole 12 by turning a knob 20 of the valve 19. In the holes 14, 15 and 16 are provided gas tube coupling nipples 21, 22 and 23. Located on the shoulder 13 is a flexible rubber check valve 24 which is in the form of a tube 25 with a crimp at one end 26 which prevents flow from the downstream side 12 to the upstream side 11. The valve 24 is held in place by a threaded retaining ring 27 the interior hole 28 of which is adapted to receive an allen wrench. The hole 11 at the upstream end of the housing 10 is provided with a threaded plug 29.

Referring to FIG. 3 the system of the present invention is illustrated. In this sytem the conduit 35 is not present. A gas outlet from the respirator 30 is connected via conduit 32 to an inlet hole 14 of the control apparatus 10. The main conduit 46 from the respirator 31 is connected to the nebulizer 38 and then via conduit 37 to the breathing apparatus 34. Outlet 15 via conduit 33 optionally powers a gas atomizer in the nebulizer 38. Conduit 33 is a direct connection to the nebulizer 38 which will power it during the inspiratory phase of the ventilatory cycle. Outlet hole 16 receives conduit 36 which separately controls the exhalation valve 40 via conduit 39. Between inlet hole 14 and outlet hole 16, is the one way check valve 24.

The purpose of control apparatus 10 is to hold pressure on the diaphragm 41 on the exhalation valve 40 after the gas pressure from the respirator 31 is released. The needle valve 19 and seat 18 assembly allows pressure to be bled off slowly from conduits 36 and 39 and the diaphragm 41, which introduces the element of time to be established for inflation hold in the lungs. Gas escapes through the needle valve 19 and seat 18 and out the hole 12 so that at some point the gas pressure on the diaphragm 41 is released.

In operation, the respirator 31 cycles into the inspiratory phase as the patient draws gas from the respirator 31. This allows gas to flow under pressure through the respirator 31 from the gas supply 30 inflating the patient's lungs. In so doing, gas is diverted via conduit 33 to power the nebulizer 38, which breaks up water into minute particles to be carried into the lungs via conduit 37 and breathing element 34.

The function of the variable inflation hold control apparatus 10 is introduced at this point in that when a pressure limit has been reached by the respirator 31 in the patient's lungs the respirator 31 pressure cycles off. The inflation hold control aparatus 10 retains gas pressure on the diaphragm 41 in the exhalation valve assembly 40. The needle valve 19 in the variable inflation hold control apparatus 10 establishes a time element which keeps the exhalation valve 40 closed until enough pressure has been released so that the diaphragm 41 of the exhalation valve 40 may be moved, thus allowing the patient to exhale passively. This modifies the usual cycling of the system, as it forces the patient to retain air within his lungs longer than normally would occur with the prior art use of a respirator 31.

This inflation hold period has proven to be of significant advantage for a number of patients receiving intermittent positive pressure breathing treatments. The control apparatus allows a timing element or inflation hold which will create an apneustic plateau following inspiration. The inflation hold time is usually from about 0.5 to 3 seconds; however, with the needle valve 19 retracted into the hole 17, the usual mode of operation with the respirator 31 can be achieved. The system with the control apparatus 10 in use is of therapeutic value for the equilibration of pressure and gases within the distal parts of the bronchial tree. It also allows a greater length of time for medication in aerosol form to be deposited in the ling further enhancing the effects of the drug. The control apparatus 10 also produces an enforced means of breathing exercise which tends to lend credence to intermittent positive pressure breathing treatments. Thus the control apparatus enhances respiratory therapy by providing a tool that can be utilized not only for breathing exercise, but for proper distribution of gas and aerosol within the lung.

I claim:

1. In a system used for intermittent positive pressure lung treatment including a gas source, a first gas line, a breathing element for providing the gas to the lungs of a patient upon inspiration, respirator means providing an intermittent positive pressure from said source to said breathing element via said first gas line, a second gas line and a normally closed pressure sensitive exhaust valve means for allowing elimination of the gas upon expiration from the lungs including a valve element connected to the breathing element and a control chamber connected to the respirator via said second gas line, said valve element being responsive to a pressure within said control chamber whereby said exhaust valve element is opened at a predetermined pressure limit established in said control chamber when the pressure is released therefrom, the improvement comprising a housing having a passageway therethrough, a one way check valve mounted in said passageway, said passageway being connected into said second gas line so as to have an upstream side connected to the respirator and a downstream side connected to the respirator and a downstream side connected to the exhaust valve control chamber, a vent connected to said passageway on the downstream side of said check valve and having a variable constriction for controlling gas flow out the vent, thereby relieving the pressure in said exhaust valve control chamber to establish said predetermined pressure limit at which said exhaust valve element opens, whereby there is a delay in the opening of the exhaust valve causing gas to be held in the lungs for a period of time.

2. The apparatus of claim 1 wherein in addition the respirator provides gas to the lung through a nebulizer for providing liquid vapors in the gas to the lungs and wherein the nebulizer vaporization is provided by a direct gas bypass connection to the check valve housing on the upstream side of the check valve.

3. The apparatus of claim 1 wherein the constriction opening is regulated by a needle valve.

4. The apparatus of claim 1 wherein the check valve is a flexible rubber crimped end tube which allows gas to pass only through the tube in the direction of the crimp to the downstream side of the housing.

* * * * *